United States Patent [19]

McCormick et al.

[11] Patent Number: 5,669,390

[45] Date of Patent: Sep. 23, 1997

[54] SINGLE USE PROTECTIVE BARRIER MEDICAL ACCESSORY FOR ISOLATING A SPHYGMOMANOMETER CUFF FROM A PATIENT

[76] Inventors: David A. McCormick; Martha S. McCormick, both of 9880 E. Palermo, Gold Canyon, Ariz. 85219

[21] Appl. No.: 564,913

[22] Filed: Nov. 30, 1995

[51] Int. Cl.$^6$ ....................................................... A61B 5/00
[52] U.S. Cl. ............................................ 128/686; 606/202
[58] Field of Search ........................... 128/686, 846–849, 128/853–856, 877, 878, 821; 606/202

[56] References Cited

U.S. PATENT DOCUMENTS

| | | | |
|---|---|---|---|
| 4,548,249 | 10/1985 | Slaughterbeck | 128/686 |
| 4,745,915 | 5/1988 | Enright et al. | 128/853 |
| 4,967,758 | 11/1990 | Masciarotte | 128/686 |
| 5,070,544 | 12/1991 | Aliberti et al. | 2/170 |
| 5,143,762 | 9/1992 | Ho | 428/35.7 |
| 5,228,448 | 7/1993 | Byrd | 128/686 |
| 5,392,786 | 2/1995 | Lewis et al. | 128/877 |
| 5,411,518 | 5/1995 | Goldstein et al. | 128/686 |
| 5,433,221 | 7/1995 | Adair | 128/853 |
| 5,513,643 | 5/1996 | Suite | 128/686 |

OTHER PUBLICATIONS

Melco, Inc.—1995 Catalog, p. 12, items 1806, 1807, 1808.

*Primary Examiner*—Robert Nasser
*Attorney, Agent, or Firm*—James H. Phillips

[57] ABSTRACT

A single use protective barrier medical accessory serves to isolate a sphygmomanometer cuff from a patient whose blood pressure is to be taken in order to prevent contamination of the cuff by the patient's bodily fluids such as blood. The medical accessory constitutes an open ended tubular sleeve fabricated from readily foldable, fluid impervious material. Each open end is provided with an elastic band to snugly close around the patient's arm. In use, the tubular sleeve is introduced over a patient's arm and slid into position. A sphygmomanometer cuff is then fixed in place over the sleeve in the usual position on the patient's arm. Then, an upper portion of the sleeve is folded over to completely cover the sphygmomanometer cuff while permitting admission of a tube coupled to a bulb for pressurizing the cuff. After the patient's blood pressure has been taken, the upper portion is unfolded, the cuff is removed and the sleeve is removed and disposed of, preferably according to established procedures. In one preferred embodiment, the upper portion of the sleeve includes a window through which a gauge attached to the cuff may be read.

7 Claims, 1 Drawing Sheet

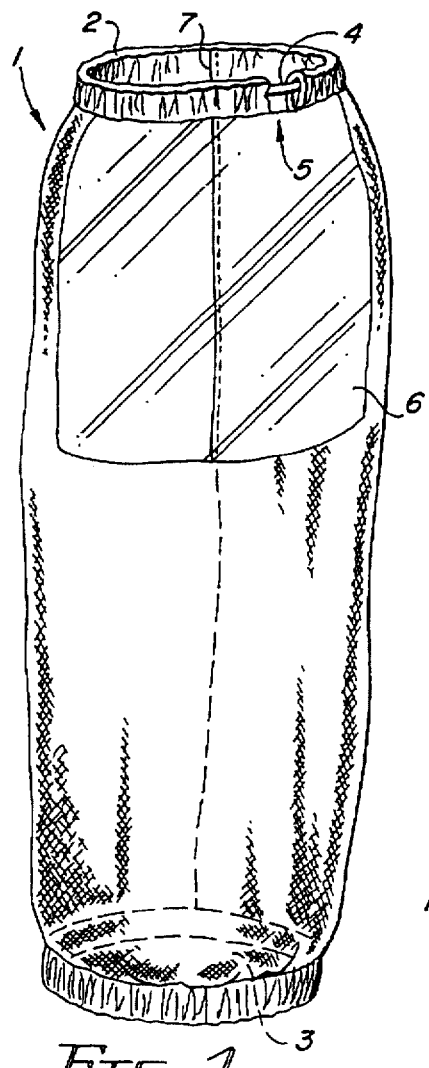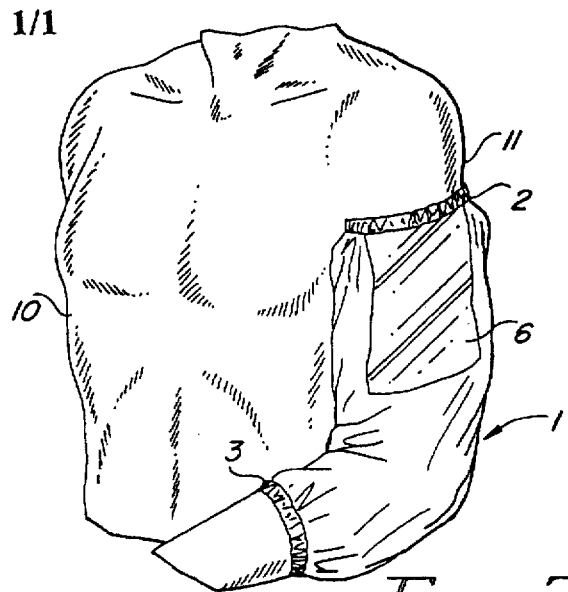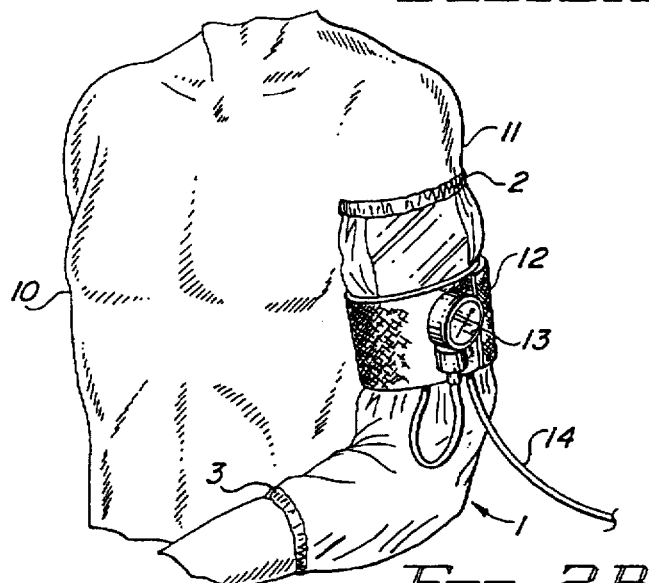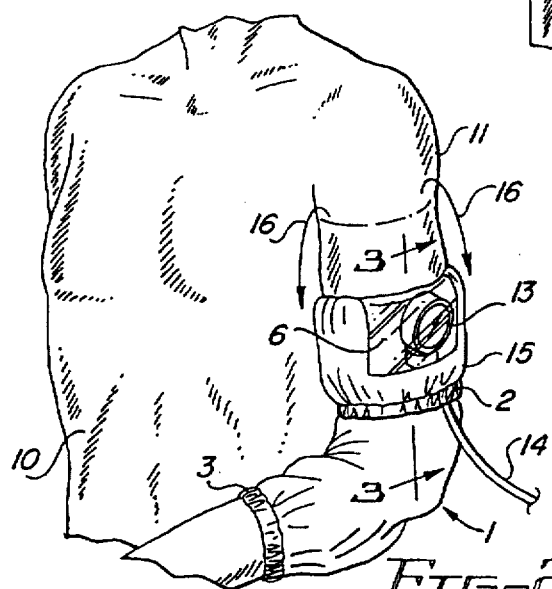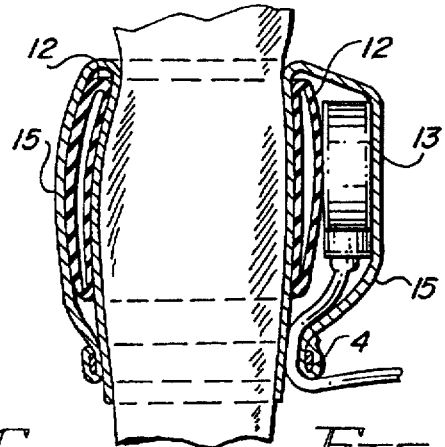

SINGLE USE PROTECTIVE BARRIER MEDICAL ACCESSORY FOR ISOLATING A SPHYGMOMANOMETER CUFF FROM A PATIENT

FIELD OF THE INVENTION

This invention relates to the medical arts and, more particularly, to a single use protective barrier medical accessory for isolating a sphygmomanometer cuff from a patient in order to prevent contamination of the patient, the sphygmomanometer cuff and one or more subsequent patients whose blood pressure is taken with the same sphygmomanometer.

BACKGROUND OF THE INVENTION

One of the most common medical diagnostic procedures is taking a patient's blood pressure. This pressure depends upon interrelations between a number of factors, the important ones being: (1) the force of contraction of the left ventricle of the heart as it pumps forth blood; (2) the volume of blood forced into the aorta by the contraction of the left ventricle; (3) the peripheral resistance of the arteries, their elasticity and tone; and (4) the viscosity of the blood. Both systolic and diastolic pressures are measured. The systolic indicates the pressure during systole, when the heart is contracting and forcing out blood, while the diastolic indicates the pressure during diastole, when the heart muscle is relaxed and its chambers are filling with blood. The normal systolic values are given as 100 to 140 mm. of mercury, and the diastolic as 60 to 90 mm. of mercury. These figures vary with age, exercise, degree of obesity and emotional stress such that there is a substantial variability to the normal range.

While blood pressure readings are always of importance to a medical practitioner accessing the condition of a patient, it may be a critical early indicator in emergency conditions such as those encountered in the emergency rooms of hospitals, or even more so, at accident scenes where persons have been injured. One common and distressing example of the latter is at the site of a motor vehicle accident which has caused the injury of several persons. Many government and private organizations include special units for responding to the occurrence of accidents and other emergencies which result in injury to persons by transporting paramedics and/or other trained medical practitioners to the scene as quickly as possible. Typically, as soon as possible under the circumstances, the blood pressure of each victim at an emergency site will be taken to obtain an indication of their respective conditions, and the results of these blood pressure readings are one of the indicators for taking specific subsequent action as to each victim.

Blood pressure is taken with a sphygmomanometer which consists of an inflatable cuff which is wrapped around the upper arm. This cuff is inflated by a hand bulb. The cuff is connected by tubing to a measuring device which is either a sealed column of mercury or a spring scale, often in the form of a gauge fixed to the cuff. Sufficient pressure is pumped into the cuff to compress the brachial artery in the upper arm. A stethoscope is applied over the artery below the cuff, and air is gradually allowed to escape from the cuff until the pulse can be heard. The reading on the gauge at this point indicates the systolic pressure or the highest pressure in the artery during contraction of the heart. The deflation of the cuff is continued, and that point on the scale when the last sound of the disappearing pulse is heard is the diastolic pressure or lowest pressure in the artery during diastole.

In taking the blood pressure readings of a plurality of victims at an emergency site, a paramedic will move from victim to victim as quickly as possible and will employ the same sphygmomanometer. This unavoidable practice, however, creates a separate, potentially independently dangerous, condition. It is possible, under these conditions, to unintentionally transfer a body fluid, typically blood, from one patient to a succeeding patient, the transport mechanism being the sphygmomanometer cuff. The seriousness of this potentiality has become notoriously well known in recent years because, among others, the virus family which causes acquired immunity deficiency syndrome or AIDS may be spread in this manner. Thus, those skilled in the medical arts will recognize that it would be highly beneficial to provide an artifice for effectively preventing such transfer of viruses during the serial use of a sphygmomanometer, and it is to that end that the present invention is directed.

OBJECTS OF THE INVENTION

It is therefore a broad object of this invention to provide apparatus for protecting a sphygmomanometer cuff against contamination from body fluids while taking a patient's blood pressure.

It is a more specific object of this invention to provide a medical accessory which is introduced over the arm of a patient whose blood pressure is to be taken prior to placing a sphygmomanometer cuff over the accessory in order to provide fluid and viral isolation between the patient and the cuff during the blood pressure determination process.

It is a still more specific object of this invention to provide such a medical accessory in the form of a tubular sleeve which serves to substantially isolate a sphygmomanometer cuff during use while still permitting access to the cuff for inflation and a view of the gauge to take the reading.

In another aspect, it is an object of this invention to provide such a medical accessory which is inexpensive to fabricate, easy to use, certain and fast in operation and disposable after a single use in order to permit serial blood pressure readings to be taken from a plurality of patient's with the same sphygmomanometer while substantially limiting the potential for cross contaminating a patient with another patient's body fluids inadvertently deposited on a sphygmomanometer cuff.

SUMMARY OF THE INVENTION

Briefly, these and other objects of the invention are achieved by providing a single use protective barrier medical accessory for isolating a sphygmomanometer cuff from a patient whose blood pressure is to be taken. The medical accessory constitutes an open ended tubular sleeve fabricated from readily foldable, fluid impervious material, the tubular sleeve being sufficiently long to extend from beneath a patient's armpit to a point below the patient's elbow and having a circumference sufficient to admit of ready introduction over the patient's arm. Each of the upper and lower open ends of the sleeve are provided with elastic bands adapted to snugly close the ends around the patient's arm. In use, the tubular sleeve is introduced over a patient's arm and slid into position for use. A sphygmomanometer cuff is then fixed in place over tubular sleeve in the usual position on the patient's arm. Then, an upper portion of the tubular sleeve is folded over to completely cover the sphygmomanometer cuff while permitting admission of a tube coupled to a bulb for pressurizing the cuff. After the patient's blood pressure has been taken, the upper portion is unfolded to its original position, a the sphygmomanometer cuff is removed and the tubular sleeve is removed and disposed of, preferably according to established procedures.

In one preferred embodiment, the upper portion of the tubular sleeve includes a window through which a gauge attached to the sphygmomanometer cuff may be read. In another embodiment, for use in permanent installations in which the sphygmomanometer gauge or manometer is wall-mounted, the entire tubular sleeve may be fabricated from a single opaque material. In yet another embodiment, the entire tubular sleeve may be fabricated from a single transparent material.

DESCRIPTION OF THE DRAWING

The subject matter of the invention is particularly pointed out and distinctly claimed in the concluding portion of the specification. The invention, however, both as to organization and method of operation, may best be understood by reference to the following description taken in conjunction with the subjoined claims and the accompanying drawing of which:

FIG. 1 is a pictorial view of one presently preferred embodiment of the invention;

FIG. 2A is a partial pictorial view illustrating a first step in the use of the invention;

FIG. 2B is a view similar to FIG. 2A illustrating a second step in the use of the invention;

FIG. 2C is another view similar to FIG. 2A illustrating a third step in the use of the invention; and FIG. 3 is a cross sectional view taken along the lines 3—3 of FIG. 2C showing certain of the special structure of one presently preferred embodiment of the invention.

DESCRIPTION OF THE PREFERRED EMBODIMENT(S)

Referring now to FIG. 1, there is shown one presently preferred embodiment of the invention. A single use protective barrier medical accessory for isolating a sphygmomanometer cuff from a patient whose blood pressure is to be taken constitutes a specially configured tubular sleeve 1. The tubular sleeve 1, which is generally cylindrical in shape, is fabricated from readily foldable, fluid impervious material for reasons which will be set forth in more detail below. The tubular sleeve 1 includes a first open end 2 and a second open end 3. Each open end 2, 3 is provided with cincture structure, preferably in the form of an elastic band 4, which is completely encompassed by the foldable, fluid impervious material as at 5.

Preferably, but not necessarily in all contemplated uses, a transparent window 6 is incorporated into the tubular sleeve 1 to extend from a position proximate the first open end 2 downwardly toward the second open end 3. The window 6 need not continue about the complete circumference of the tubular sleeve 1 and preferably extends somewhat less than half way around. As will be explained more fully below, the window 6 is integrated with the fluid impervious material 5 such that the seams therebetween are rendered fluid tight as by the continuous use of an adhesive about the periphery of the adjoining areas. This aspect of this embodiment of the invention will be discussed further below in conjunction with the description of FIG. 3. In a variant configuration, as will also be discussed further below, the entire tubular sleeve, except for the elastic bands 4, may be fabricated from transparent material having the requisite strength and fluid impermeable characteristics.

While the tubular sleeve 1 may be fabricated from seamless tubular material, one presently preferred method of fabrication involved bringing together opposing edges of a generally rectangular sheet of the fluid impervious material and joining the edges at a seam 7. The seam 7 should be configured, as, for example, by the use of a double fold, to join the two edges in a substantially fluid impervious manner.

Attention is now directed to FIG. 2A which shows a partial pictorial view illustrating a first step in the use of the invention. In preparation for taking the blood pressure of a patient 10, the tubular sleeve 1 is slipped over the arm 11 of the patient and is pulled upwardly into a preliminary functional position at which the first end 2 is situated at about the upper terminus of the patient's arm; i.e., just under the arm pit. The tubular sleeve 1 is oriented such that the transparent window 6 is at the top and facing generally outwardly more or less as shown. The elastic bands at the ends 2, 3 each serve as a cincture to snugly hold the tubular sleeve in place and to impede the inadvertent introduction of body fluids through the sleeve end regions.

The next step in the use of the invention is illustrated in FIG. 2B An inflatable sphygmomanometer cuff 12 is introduced over the tubular sleeve 1 around the arm of the patient 10 in the region just above the patient's elbow. As is well known to those skilled in the art, this step is typically accomplished by enwrapping the cuff 12 about the patient's arm and snugly securing it using mating hook and loop fasteners or the functional equivalent. The cuff 12 may carry a gauge 13 which will subsequently be used to take the blood pressure readings in the well known manner. A robe 14 leads from the interior of the inflatable cuff 12 to a bulb (not shown) which is used to inflate the cuff.

The next step in the use of the invention is shown in FIG. 2C. An upper portion 15 of the tubular sleeve 1 is folded downwardly over the sphygmomanometer cuff 12, as indicated by the arrows 16, in such a manner that the previously inside surface of the portion 15 of the sleeve 1 is now disposed over the cuff 12 and facing outwardly, thereby protecting the cuff against contamination by body fluids. In this position, as best shown in FIG. 2C, the gauge 13 may readily be observed through the portion of the window 6 which has been folded downwardly with the rest of the upper portion 15 of the tubular sleeve 1. At this point, the patient's blood pressure may be taken by suitably inflating the cuff 12 via the tube 14 and conventionally subsequently releasing the pressure while observing the readings on the gauge 13 in the manner previously described.

It will be observed that, during the entire procedure, the sphygmomanometer cuff has been effectively isolated from the patient 10 and from any body fluids, such as blood, which may be present on his person which could contaminate the cuff 12. The use of the subject invention in the manner shown particularly in FIG. 2C ensures that the sphygmomanometer cuff is protected by a viral and fluid resistant barrier while facility of operation and accuracy of the procedure are unimpaired.

FIG. 3 illustrates this operational isolation particularly well. The cuff 12, shown inflated, and the gauge 13 are completely protected from body fluids while the procedure may readily be carried out by viewing the gauge 13 through the window 6 as previously discussed. The elastic band 4 serving to effectively close off access by such bodily fluids to the cuff 12 as a result of the foldover step.

When an individual patient's blood pressure has been taken, the portion 15 of the tubular sleeve 1 is folded back up to the same position as shown in FIG. 2B, the sphygmomanometer cuff 12 is removed and the tubular sleeve is pulled off the patient's arm and disposed of according to established procedures which take into account possible contamination. The blood pressure of a subsequent patient may immediately be taken up using the same sphygmomanometer cuff 12 in conjunction with a new, sterile tubular sleeve 1. In this manner, the chances of infecting or otherwise contaminating one patient with another patient's body fluids during a series of blood pressure procedures is greatly diminished.

Those skilled in the medical arts will appreciate that there are types of sphygmomanometer which do not employ a gauge situated adjacent or fixed to the cuff. Rather, particularly in permanent installations, the sphygmomanometer gauge or manometer may be fixed to a nearby wall for convenience. Thus, a variant configuration of the invention is contemplated for such applications which, typically, are to be found in a hospital or a doctor's office. For these applications, the window 6 may be omitted such that the entire tubular sleeve 1 may be fabricated from the readily foldable, fluid impervious material. The advantage of this variant, in those environments in which the sphygmomanometer gauge or manometer are remote from the cuff, is that it is simpler and less expensive to make considering the omission of the window.

In a second contemplated variant, the entire tubular sleeve 1 may be fabricated from a transparent material having the requisite strength and fluid impervious characteristics. This second variant is equally usable with either type of sphygmomanometer.

It will be clear from the foregoing that the selection of the materials used in the fabrication of the invention, and the fabrication techniques themselves, are of the highest importance. An especially well adapted material which is presently commercially available for use as the foldable, fluid impervious material is DuPont Tyvek® BarriStat® which provides excellent resistance against blood, body fluids and viral contaminants and provides splash protection against many liquid chemicals. This tough barrier fabric has exemplary strength and durability to resist punctures and tears during extensive contact under pressure. It is made of submicron denier high density polyethylene filaments that are spun and bonded together by heat and pressure and coated to meet ASTM standards ES21 (visual penetration) and ES22 (viral penetration) currently in effect. The clear component or material, whether for a window or for a complete tubular sleeve, may be polyethylene film of sufficient thickness, although numerous other clear, pliable plastic materials are also suitable.

Another consideration is the size of the tubular sleeve with respect to a given patient whose blood pressure is to be taken. For example, it will be apparent that an adult size tubular sleeve is not appropriate for use on an infant. Therefore, it is contemplated that the tubular sleeve be available in a modest range of sizes which preferably include at least an adult size, a child's size and an infant's size.

Thus, while the principles of the invention have now been made clear in an illustrative embodiment, there will be immediately obvious to those skilled in the art many modifications of structure, arrangements, proportions, the elements, materials, and components, used in the practice of the invention which are particularly adapted for specific environments and operating requirements without departing from those principles.

What is claimed is:

1. A single use protective barrier medical accessory for isolating a sphygmomanometer cuff from a patient whose blood pressure is to be taken, said medical accessory comprising a tubular sleeve including a first portion fabricated from readily foldable, fluid impervious, non-transparent material, said tubular sleeve having a first open end and a second open end, said tubular sleeve being sufficiently long to extend from about the upper terminus of a patient's arm to a point below said patient's elbow, said tubular sleeve further including a second, transparent window portion extending from proximate said first end to a point intermediate said first open end and said second open end, said tubular sleeve having a circumference sufficient to admit of ready introduction of said tubular sleeve over said patient's arm and into a functional position extending from about the upper terminus of said patient's arm to a point below said patient's elbow, said first and second open ends of said tubular sleeve each being provided with cincture means adapted to snugly close said first and second ends around said patient's arm to thereby maintain said tubular sleeve in position during use; whereby, sequentially, said tubular sleeve may be introduced over an arm of said patient and slid into position for use with said window portion facing generally outwardly, a sphygmomanometer cuff may be emplaced over said tubular sleeve above said patient's elbow, a segment of said tubular sleeve extending between said sphygmomanometer cuff and said first open end of said tubular sleeve may be folded over said sphygmomanometer cuff for complete coverage thereof, for a view of a gauge thereof through said window portion while permitting admission of a tube coupled to a bulb for pressurizing said sphygmomanometer cuff, said patient's blood pressure may be taken, said segment may be unfolded to its original position, said sphygmomanometer cuff may be removed and said tubular sleeve may be removed and disposed.

2. The single use protective barrier medical accessory of claim 1 in which said cincture means at each of said first and second ends thereof comprises a circumferential elastic band completely encompassed by said foldable, fluid impervious material.

3. The single use protective barrier medical accessory of claim 2 which includes a longitudinal seam extending between said first and second ends of said tubular sleeve, said longitudinal seam being substantially fluid impervious.

4. The single use protective barrier medical accessory of claim 2 in which said foldable, fluid impervious material comprises high density polyethylene and has at least the splash and viral barrier protection specified by ASTM standards ES 21 and ES 22.

5. The single use protective barrier medical accessory of claim 1 which includes a longitudinal seam extending between said first and second ends of said tubular sleeve, said longitudinal seam being substantially fluid impervious.

6. The single use protective barrier medical accessory of claim 5 in which said foldable, fluid impervious material comprises high density polyethylene and has at least the splash and viral barrier protection specified by ASTM standards ES 21 and ES 22.

7. The single use protective barrier medical accessory of claim 1 in which said foldable, fluid impervious material comprises high density polyethylene and has at least the splash and viral barrier protection specified by ASTM standards ES 21 and ES 22.

* * * * *